United States Patent [19]

Bonnet

[11] Patent Number: 4,712,547

[45] Date of Patent: Dec. 15, 1987

[54] INSTRUMENT FOR SLITTING STENOSES IN BODILY PASSAGES

[76] Inventor: Ludwig Bonnet, Jahnstrasse 28, 7134 Knittlingen, Fed. Rep. of Germany

[21] Appl. No.: 67,431

[22] Filed: Jun. 25, 1987

Related U.S. Application Data

[63] Continuation of Ser. No. 862,690, May 13, 1986, abandoned.

[30] Foreign Application Priority Data

Jun. 7, 1985 [DE] Fed. Rep. of Germany ....... 3520524

[51] Int. Cl.$^4$ ............................................. A61B 17/32
[52] U.S. Cl. ..................................... 128/311; 128/305
[58] Field of Search ................... 128/305, 305.1, 311, 128/751, 310, 753, 754, 304; 604/32

[56] References Cited

U.S. PATENT DOCUMENTS

| | | | |
|---|---|---|---|
| 518,600 | 4/1894 | Hallman | 128/311 |
| 749,689 | 1/1904 | Houghton | 128/311 |
| 1,127,948 | 2/1915 | Wappler | 128/311 X |
| 1,677,337 | 7/1928 | Grove | 128/305.1 |
| 2,541,246 | 2/1951 | Held | 128/305 |
| 2,655,154 | 10/1953 | Richter | 128/305 |
| 4,627,436 | 12/1986 | Leckrone | 128/305 X |

FOREIGN PATENT DOCUMENTS

| | | | |
|---|---|---|---|
| 2737014 | 3/1979 | Fed. Rep. of Germany | 128/311 |
| 3231127 | 2/1984 | Fed. Rep. of Germany | 128/305 |
| 759098 | 8/1980 | U.S.S.R. | 128/305 |

Primary Examiner—Michael H. Thaler
Attorney, Agent, or Firm—Hill, Van Santen, Steadman & Simpson

[57] ABSTRACT

An instrument such as a ureterotome for slitting stenoses in bodily passages. A shaft for inserting into the ureter has a blade set in a distal shaft portion. During insertion the blade projects axially with a distal rounded-off cutter extremity out of the shaft this being its inoperative position. When the shaft is in place the blade may be outwardly pivoted through a distally open longitudinal slot of the shaft by means of a proximal handle and of a traction wire. The shaft being traversed laterally beside the blade by a passage for passing through a guiding wire by means of which the ureterotome is introduced into the ureter.

17 Claims, 5 Drawing Figures

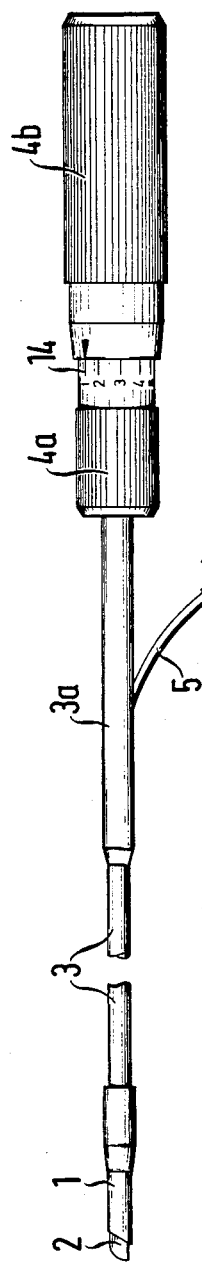
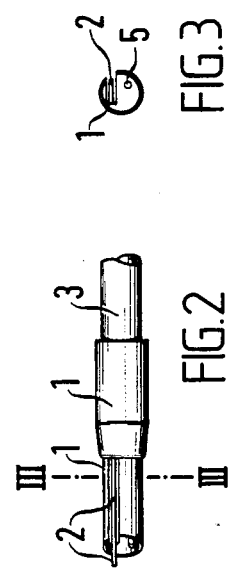
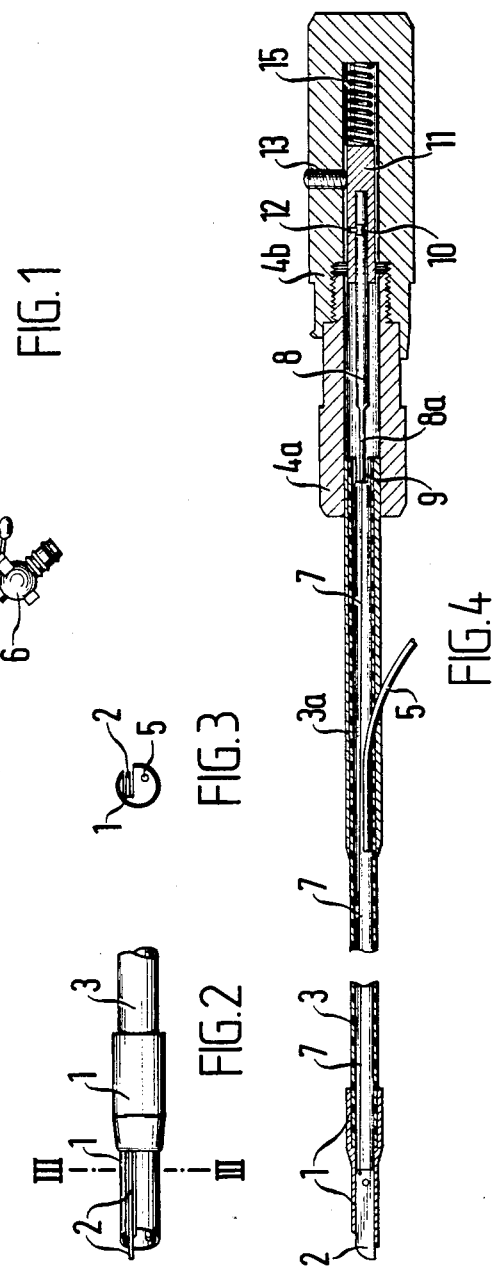
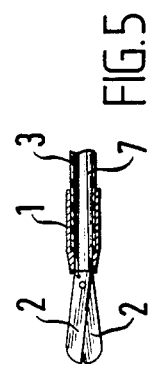

INSTRUMENT FOR SLITTING STENOSES IN BODILY PASSAGES

This is a continuation of application Ser. No. 862,690 filed May 13, 1986, now abandoned.

BACKGROUND OF THE INVENTION

The invention relates to an instrument for slitting stenoses in bodily passages, in which a shaft is traversed by a traction wire intended to be manipulated from the proximal end of the shaft for lateral outward pivoting of a blade mounted at the distal end of the shaft.

DESCRIPTION OF THE PRIOR ART

It is known that stenoses in the ureter may be slit once or several times to different depths by means of a distal blade outwardly pivotable from the shaft of an instrument, so that a clear passage through the ureter may be re-established (e.g. see U.S. Pat. No. 518,600 and German utility model No. 7,727,487). These known rigid instruments have a limited length and are consequently appropriate only for stenoses in the ureter, also because of their diameter.

A ureterotome (DE-OS No. 32,31,127) comprising a flexible shaft is also known, which is traversed by a passage for a flexible guiding catheter, so that the shaft may have its distal blade fed blind to a stenosis in the ureter, which is to be slit. This blade should be covered by a cap, increasing the shaft diameter upon being passed through a ureter, so that the passing through of the shaft through the narrow ureter is at least rendered more difficult. In view of the rigid fixed position of the blade, a modification of the frequently required cutting depth of the stenosis which is to be slit is also impossible.

SUMMARY OF THE INVENTION

It is an object of the invention to provide an instrument by means of which stenoses or annular constrictions in the ureter may be cut open without damage to the ureter, notwithstanding its curved extension, to assure the outflow of urine from the kidney into the bladder.

According to the invention, this object is achieved in that for slitting stenoses in the ureter, the blade set in the inoperative position projects axially with a rounded-off distal cutter extremity out of the distal extremity of the shaft which is to be led through the ureter, and may be pivoted outwards through a distally open elongate slot of the shaft by means of a proximal handle and a traction wire, and in that laterally beside the blade, the shaft is traversed by a passage which may be used for passing through a guiding wire, a flexible optical system comprising fibre light and fibre image guides for introduction of a contrast medium, into the ureter, or for infeed and discharge of a flushing liquid into and out of the ureter.

Thanks to this solution, it is possible for the ureterotome according to the invention to have its distal extremity, with the blade connected thereto, led under guidance by means of a guiding wire extending through the passage, through the urethra and the bladder and into the ureter as far as the stenosis, to which end a visual check may also be undertaken by means of a flexible optical system which may be led through the passage of the ureterotome. If the guiding wire then replaces the optical system the blade projecting distally in the axial direction can be prevented from injuring the ureter, the extension of which differs from the rectilinear and may differ considerably therefrom. It is equally also possible to offer the ureterotome up to the stenosis via a nephroscope.

As soon as the stenosis has been reached, and if its diameter is too tight to allow traversal by the shaft, the distally projecting blade will slit the stenosis to the required minimum diameter during the continued forward feed of the ureterotome, so that the shaft may then be led through the stenosis. The blade is thereupon outwardly pivoted by actuation of the handle and then retracted rearwards with the shaft, when the stenosis is slit open to the required depth as a function of the outwardly pivoted angle of the blade. This action may be repeated several times. It is also possible to introduce a contrast medium via the passage of the shaft, to allow an X-ray examination.

Further objects and advantages of this invention will become apparent from the following detailed description taken in conjunction with the accompanying drawings.

BRIEF DESCRIPTION OF THE DRAWINGS

FIG. 1 shows a sideview of a ureterotome for slitting stenoses in the ureter of a patient, FIG. 2 is an enlarged view of the distal shaft extremity of the ureterotome seen at right angles to the sideview of FIG. 1, FIG. 3 shows a cross-section along the line III—III of FIG. 2, FIG. 4 shows an axial longitudinal cross-section through the ureterotome according to FIG. 1, and FIG. 5 shows the distal part of FIG. 4 with incorporation of two blades.

DETAILED DESCRIPTION OF THE PREFERRED EMBODIMENTS

The ureterotome according to the invention, intended for back-stroke stenosis slitting, comprises a shaft having a rigid distal portion 1 for reception of a pivotally mounted blade 2, and a flexible shaft portion 3 which is secured in a proximal handle element 4a via an element 3a. The shaft 1, 3, 3a is traversed by a passage 5 which is led out of the shaft portion 3 at its proximal end and is provided with a shut-off valve 6. The blade 2 projects with a distal rounded-off cutter portion axially out of the distal extremity of the rigid shaft portion 1, and the shaft portion 1 is provided with a distally open longitudinal slot along the blade length. For its lateral outward pivoting through the longitudinal slot of the shaft portion 1, the blade 2 is connected to a traction wire 7 which merges proximally into a traction rod 8, which is flattened at its distal end 8a and untwistably traverses a guiding element 9. The rod 8 is provided with an annular groove 10 in its proximal end portion and is held by a rotary element 11 through which extends a radial pin 12 engaging in the annular groove 10, so that the rotary element 11 is rotatably retained on the traction rod 8. On the other hand, the rotary element 11 is connected securely and releasably to the handle element 4b by means of a radial screw 13 extending through the rotatable handle element 4b from the outside. The handle element 4b may be screwed on to the proximal extremity of the handle element 4a, the angular position of the blade 2 being readable on a scale 14. The longitudinal displacement of the portion 4b in the proximal direction resulting from the spiral rotary displacement, leads to a proximal pull on the traction wire 7,8 and thus to lateral outward pivoting of the blade 2 from the shaft portion 1. The adjustable pivoting angle determines the cutting depth of the blade 2 in the annular stenosis.

For application of the ureterotome, a guiding wire is passed through passage 5, and the ureterotome is then inserted along the wire through the urethra and the bladder into the ureter, until the distal extremity has reached the stenosis in the ureter. If the passage through the stenosis is too narrow, the ureterotome is pushed in distal direction under appropriate pressure, and whilst doing so, the distally projecting blade portion will slit the stenosis open to at least the diameter of the shaft element 1. As soon as the blade is distally positioned behind the stenosis, it is outwardly pivoted from the shaft extremity by twisting the handle element 4b, and the ureterotome is retracted so that the stenosis is slit open on the back stroke, that is to say to the depth required in each case, by means of the blade positioned at an angle. This operation may be repeated several times.

The screw 13 which is a knurled screw in the case of a partially flexible shaft, is loosened before and after performing the stenosis slitting operation, so that the blade 2 may be set at its inoperative position via the guiding wire 7,8 by means of the compression spring 15 housed in the handle element 4b, so that the ureterotome may be led into the ureter without danger. The releasable connection by means of the knurled screw 13 and of the spring 15 are required in the case of a shaft comprising a flexible section, since bending actions during insertion into the ureter cause axial changes in the position of the traction wire extremity which have to be counteracted to prevent outward pivoting of the blade.

In the case of the embodiment illustrated, it is also possible for several blades 2, e.g. two blades, to be installed mutually parallel according to FIG. 5, e.g. so that they may be pivotable and pivoted in opposite outward directions in mirror symmetry.

If a rigid ureterotome is utilised to slit a stenosis or may be so utilised, the said spring 15 merely has the task of placing the blade 2 in the inoperative position once via the traction wire 7,8 during assembling. To this end, the screw 13 which may then also be a grub screw or the like, should first be screwed in to the securing position for the traction wire, after the inoperative position of the blade has been set by means of the spring 15.

What is claimed is:

1. An instrument for slitting stenoses in bodily passages, comprising:
    hollow shaft having proximal and distal ends, said distal end being open; a rigid blade receiving portion having a lateral extent and mounted to said distal end of hollow shaft;
    a blade mounted in said blade receiving portion, said blade having a rounded-off distal cutting extremity and a lateral cutting edge at one lateral edge and being pivotble outwardly from an axial cutting position in which said blade projects axially beyond the distal extremity of said blade receiving portion of said instrument to a lateral cutting position with said lateral cutting edge extending laterally of the bladle receiving portion through a distal end longitudinal slot in said blade receiving portion, said blade when in said axial cutting position having a lateral extent greater than one half said lateral extent of said rigid blade receiving portion and effective to form a passage through a stenosis sufficient to pass said blade receiving portion;
    at least one traction wire operatively connected to said blade and extending longitudinally through said shaft for proximal actuation of said blade;
    a traction rod non-rotatably arranged in said shaft and connected to a proximal end of said at least one traction wire;
    a cylindrical extension connected to said traction rod and rotatable with respect to said traction rod
    a proximal handle threadably rotatable with respect to said shaft and connected to said cylindrical extension for operative connection to said traction wire;
    a scale on one of said shaft and said handle and a marker on the other of said shaft and said handle to indicate the threaded position of said handle relative to said shaft; and
    a longitudinal passage through said shaft to receive a guide wire for guiding said shaft through said bodily passage, said longitudinal passage allowing removal of said guide wire when said shaft is in position to clear a passage.

2. An instrument as claimed in claim 1, wherein said shaft is of rigid construction and wherein the rotatable extension of the traction rod is firmly joined to the screwable handle element.

3. An instrument as claimed in claim 1, wherein said shaft comprises a rigid distal shaft portion receiving the blade and an adjacent flexible shaft portion and wherein the traction wire has a traction rod releasably connected to the screwable handle portion and spring-biassed in the distal direction.

4. An instrument as claimed in claim 1, wherein the handle is screwable to actuate said blade and has allocated to it a scale of a handle element firmly joined to the shaft, on which may be read the degree of twist of the handle and hence the axial traction wire displacement and the outward pivoting of the blade.

5. An instrument as claimed in claim 1, wherein said distal shaft end has at least two blades arranged therein, which are outwardly pivotable in a radial direction around appropriate pivot bearings by means of at least one said traction wire.

6. An instrument as claimed in claim 1, wherein said instrument is in the form of a ureterotome.

7. An instrument having distal and proximal ends for slitting stenoses in an interior body passageway through which a guide wire is passed comprising:
    a handle at the proximal end and a blade carrying member having a lateral extent at the distal end,
    a shaft member intermediate the proximal and distal ends,
    a slitting blade carried by said blade carrying member adjacent said distal end, the slitting blade projecting from an open end of said blade carrying member at said distal end, said blade pivotable between a first position where said blade projects axially beyond said blade carrying member to a second position where said blade projects laterally of said blade carrying member and at an angle to said shaft, said blade when in said first position having a lateral extent greater than one half said lateral extent of said blade carrying member and effective to form a passage through a stenoses sufficient to pass said blade carrying member, an actuation wire having a distal end thereof connected to said blade and a proximal end thereof operatively connected to a portion of said handle, means for moving said actuation wire wherein movement of said wire is effective to pivot said blade between said positions of said blade, a channel extending through said shaft and opening out said distal end adjacent said slitting blade, said channel being ported to an exterior of said shaft spaced from said distal end towards said proximal end, said channel being dimensioned to receive the guide wire for guiding said shaft within said passageway, said guide wire exiting said channel at said port.

8. A device according to claim 7 wherein said handle has first and second portions, the first portion affixed to said shaft, the second portion being movable with respect to said first portion and said activator wire attached to said second portion of said handle.

9. A ureterotome for slitting stenoses in a ureter, comprising:

an elongated flexible shaft having first and second opposite ends and a passage extending along the longitudinal extent of said shaft, said first end having a slot laterally of said passage and defining an endmost portion of said ureterotome;

a blade pivotally mounted at said first end of said shaft in said slot for movement between a first position extending axially beyond said endmost portion of said ureterotome and a second position angularly related to said first position and extending laterally to one side of said shaft, a first cutting edge of said blade being directed out said first end of said ureterotome when said blade is in said first position to slit a stenoses open wide enough to admit said ureterotome when said shaft is moved axially against the stenoses, a second cutting edge of said blade being sheathed in said slot when said blade is in said first position and extending from said slot laterally of said shaft when said blade is in said second position; and means at said second end of said shaft for selectively moving said blade between said first position and said second position.

10. A ureterotome as claimed in claim 9, wherein said first cutting edge of said blade extends to said second cutting edge by a rounded cutting edge.

11. A ureterotome as claimed in claim 9, wherein said blade moving means includes:

a traction wire connected at a first end to said blade and extending to said content of said shaft along said passage, and threaded means for selectively adjusting the longitudinal position of said traction wire relative to said shaft to cause angular movement of said blade.

12. A ureterotome as claimed in claim 11, further comprising:

a traction rod connected to an end of said traction wire at said second end of said shaft, said traction rod having a flattened portion;

a guide element mounted at said second end of said shaft and having a shaped restricted opening through which extends said flattend portion of said traction rod to prevent said traction rod from rotating; and a handle threadably mounted at said second end of said shaft for threaded movement in an axial direction, said handle being rotationally connected dto said traction rod to cause longitudinal movement of said traction wire upon threaded movement of said handle.

13. A ureterotome as claimed in claim 12, wherein said traction rod includes anannular groove, further comprising:

a rotary element rotationally engaging said annular groove in said traction rod and disposed within said handle;

a grub screw threadably mounted in said handle and selectively engaging said rotary element; and means for biasing at least one of said traction wire and said traction rod and said rotary element in a longitudinal direction.

14. A ureterotome as claimed in claim 12, further comprising:

a scale to indicate the threaded position of said handle.

15. A ureterotome as claimed in claim 9, wherein a portion of said shaft at said first end is rigid.

16. A ureterotome as claimed in claim 9, further comprising:

a second blade pivotally mounted at said second end of said shaft substantially parallel to said first blade, said second blade having a first cutting edge being directed out of said first end of said shaft and a second cutting edge being in a direction opposite said second cutting edge of the first said blade when said blades ar ein said first position.

17. A ureterotome as claimed in claim 9, further comprising:

a shut-off valve mounted to selectively close said passage of said shaft.

* * * * *

UNITED STATES PATENT AND TRADEMARK OFFICE
CERTIFICATE OF CORRECTION

PATENT NO. : 4,712,547

DATED : December 15, 1987

INVENTOR(S) : Ludwig Bonnet

It is certified that error appears in the above—identified patent and that said Letters Patent is hereby corrected as shown below:

In column 1, line 21, change "7,727,487" to --7,725,487--.

Signed and Sealed this

Twenty-first Day of March, 1989

*Attest:*

DONALD J. QUIGG

*Attesting Officer*  *Commissioner of Patents and Trademarks*